United States Patent [19]
Ueda

[11] Patent Number: 4,799,474
[45] Date of Patent: Jan. 24, 1989

[54] MEDICAL TUBE TO BE INSERTED IN BODY CAVITY

[75] Inventor: Yasuhiro Ueda, Tokyo, Japan

[73] Assignee: Olympus Optical Co., Ltd., Japan

[21] Appl. No.: 23,636

[22] Filed: Mar. 9, 1987

[30] Foreign Application Priority Data

Mar. 13, 1986 [JP] Japan .................................. 61-55853
Jul. 16, 1986 [JP] Japan .................................. 61-165662
Sep. 2, 1986 [JP] Japan .................................. 61-206127

[51] Int. Cl.⁴ ........................ A61B 1/00; A61M 25/00
[52] U.S. Cl. ........................................... 128/4; 604/281; 604/291
[58] Field of Search ............... 128/4, 6, 400; 604/281, 604/291

[56] References Cited

U.S. PATENT DOCUMENTS

| 2,124,831 | 7/1938 | Roos ................... 128/400 X |
| 3,558,369 | 1/1971 | Wang et al. ............. 148/11.5 R |
| 3,890,977 | 6/1975 | Wilson ..................... 604/281 |
| 4,427,000 | 1/1984 | Ueda ........................ 128/6 |
| 4,601,283 | 7/1986 | Chikama ..................... 128/4 |

FOREIGN PATENT DOCUMENTS

59-2344 9/1984 Japan.

Primary Examiner—William H. Grieb

[57] ABSTRACT

A medical tube is used in an insertion portion of an endoscope and is inserted in a body cavity. The medical tube includes an outer tube having a front section, and a drive member arranged at the front section of the outer tube and having an elongated shape memory alloy adapted to have a transformation temperature such that a memorized shape is restored at the temperature higher than a temperature of heat applied to the shape memory alloy during sterilization of the medical tube.

16 Claims, 8 Drawing Sheets

MEDICAL TUBE TO BE INSERTED IN BODY CAVITY

BACKGROUND OF THE INVENTION

A. Field of the Invention

The present invention relates to a medical tube having a shape memory alloy and, more particularly, to a medical tube used in, e.g., an insertion portion of an endoscope and inserted in a body cavity.

B. Description of the Prior Art

A conventional medical tube having a shape memory alloy is disclosed in Japanese Utility Model Disclosure (Kokai) No. 59-2344. This medical tube comprises a plurality of shape memory alloys in the form of wires having a transformation temperature of 30° C. to 60° C. A power source is connected to these shape memory alloys. The shape memory alloys are energized, heated, and deformed in a predetermined direction, thereby bending the tube as a whole.

The medical tube is used while inserted in a living organism. Before the tube is used, it must be sterilized and disinfected. More specifically, the tube is usually placed in a sterilizer and sterilized using an ethylene oxide gas.

However, the temperature of the sterilizer often exceeds a transformation temperature of a shape memory alloy embedded in the tube. For this reason, the shape memory alloy in the tube tends to restore the memorized shape while it is being held in a predetermined shape in the sterilizer. Especially in a tube having a plurality of wire memory alloys, all the alloys tend to restore the memorized shapes simultaneously. As a result, the restoration force of the shape memory alloy is weakened. In other words, the shape memory alloy cannot satisfactorily restore the memorized shape. The main body of the medical tube may be damaged since the shape memory alloy tends to restore its memorized shape while being held in the predetermined position.

During aeration for eliminating the residual gas in the sterilizer after the tube is sterilized, heat having a temperature exceeding the transformation temperature of the shape memory alloy is applied to the tube. As a result, the same problem posed by sterilization occurs.

SUMMARY OF THE INVENTION

It is an object of the present invention to provide a medical tube wherein a shape memory effect (a restoration force) is not degraded and a tube body is not damaged even if heat is applied thereto while the tube is held in a predetermined position during sterilization using an ethylene oxide gas, and wherein the tube has good bending properties.

In order to achieve the above object of the present invention, there is provided a tube comprising:
an outer tube having a front section; and
a drive member arranged at the front section of the outer tube and having an elongated shape memory alloy adapted to have a transformation temperature such that a memorized shape is restored at the temperature higher than a temperature of heat applied to the shape memory alloy during sterilization of the medical tube.

The bending member, therefore, does not restore the memorized shape when the medical tube is sterilized. For this reason, the shape memory effect of the bending member is not degraded and the tube body is not overloaded, thereby preventing damage to the tube body.

DETAILED DESCRIPTION OF THE PREFERRED EMBODIMENTS

Preferred embodiments of the present invention will be described in detail with reference to the accompanying drawings.

Figure 1:
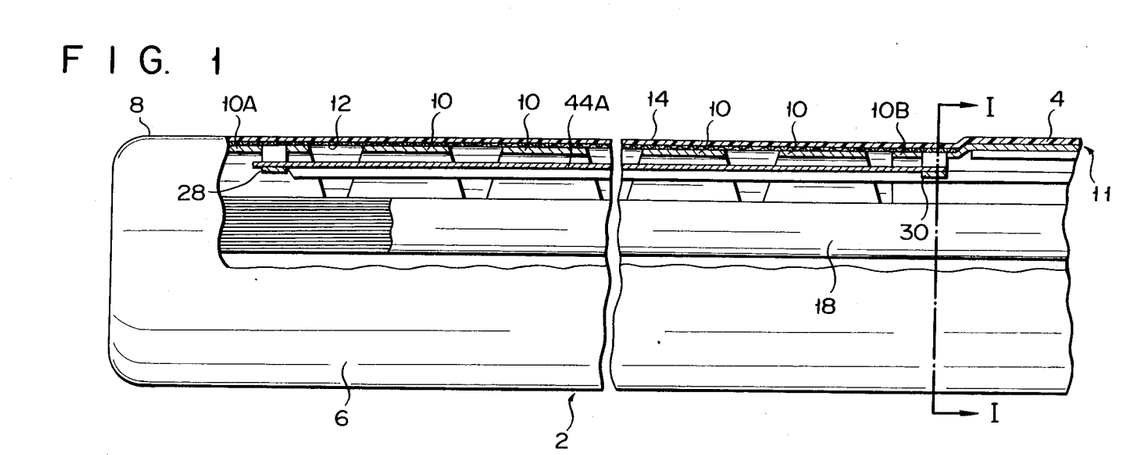
FIG. 1 is a partial cutaway enlarged side view of a front section of a medical tube according to a first embodiment of the present invention.
Figure 2:
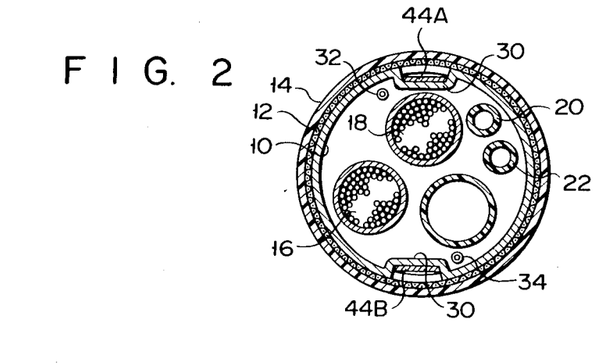
FIG. 2 is a cross-sectional view of the medical tube shown in FIG. 1 taken along the line I—I thereof.
Figure 3:
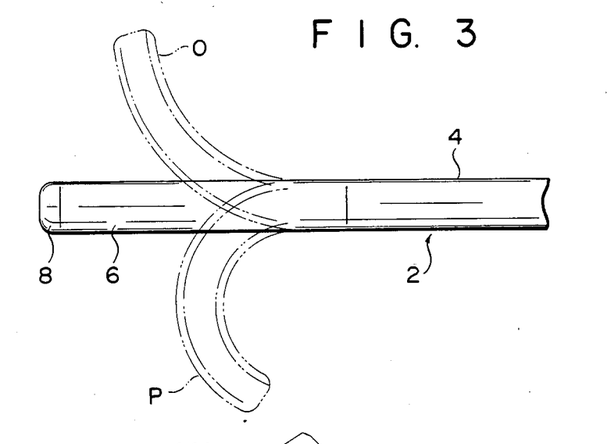
FIG. 3 is a plan view showing a state wherein the tube is bent.

FIGS. 1 to 3 show a medical tube according to a first embodiment of the present invention.

In the first embodiment, the medical tube according to the present invention is applied to insertion portion 2 of an endoscope. Insertion portion 2 comprises flexible pipe section 4, and bending pipe section or front section 6 connected to the distal end portion of pipe section 4. Distal end portion 8 is connected to the distal end of front section 6. A plurality of cylindrical joint pieces 10 are coupled to each other, as shown in FIG. 1, so that front section 6 can be bent vertically. The outer surfaces of joint pieces 10 are covered with blade or net-like pipe 12 made of stainless steel or the like. The outer surface of blade 12 is covered with sheath 14 made of a flexible material. Pipe 12 and sheath 14 compose outer tube 11 of the medical tube. As shown in FIGS. 1 and 2, image guide fibers 16, light guide fibers 18, air supply channel tube 20, and water supply channel tube 22 are inserted in outer tube 11.

First bending or drive member 44A extending along the longitudinal direction is disposed at a portion near the inner surface of joint pieces 10 of bending pipe section 6. Similarly, second bending member 44B extending along the longitudinal direction is disposed at the lower portion. Bending or drive members 44A and 44B are made of a shape memory alloy, i.e., AMS such as a Ti-Ni alloy in the form of a thin plate. Both end portions of bending members 44A and 44B are fixed to fixing portions 28 and 30 formed on frontmost and rearmost bending pieces 10A and 10B.

Lead wires 32 and 34 are respectively connected to the front and rear ends of bending members 44A and 44B. Lead wires 32 and 34 are guided to the handle portion through bending pipe section 6 and flexible pipe section 4 and are connected to power source unit 56 in FIG. 7.

As indicated by alternate long and two short dashed line O in FIG. 3, first bending member 44A memorizes an upwardly bent shape. Second bending member 44B memorizes a downwardly bent shape, as indicated by alternate long and two short dashed line P in FIG. 3.

The transformation point of each bending member 44A or 44B, i.e., the transformation point from the low-temperature martensite phase to the high-temperature austenite phase as a matrix is set to be higher than the sterilization temperature of normally 55° C. to 60° C. For example, the (As) point, i.e., the austenite transformation start temperature is set to be 65° C., and the (Af) point, i.e., the austenite transformation end temperature is set to be 70° C.

In the insertion portion of the endoscope having the arrangement described above, when distal end portion 8 is to be bent upward, as shown in FIG. 3, a current is supplied to first bending member 44A through lead wires 32 and 34, and member 44A is heated due to its electrical resistance to a temperature of 65° C. or more. Therefore, heat causes bending member 44A to bend upward. In this case, second bending member 44B is not energized and is forced to bend upward by a force (i.e., a restoration force) memorized by first bending member 44A.

However, in order to bend distal end portion 8 downward, as shown in FIG. 3, second bending member 44B is energized and heated to a temperature of 65° C. or more. As a result, member 44B is bent downward.

The insertion portion of the endoscope according to this embodiment has the following effect.

In order to insert the endoscope into a body cavity, it must be sterilized and disinfected before its use. A known, typical sterilization method uses EOG (Ethylene Oxide Gas). During sterilization, the interior of the EOG sterilizer is kept at a temperature of 55° to 60° C. or more. However, bending members 44A and 44B of this embodiment are not deformed during sterilization. Reproducibility of the bending members, i.e., reproducibility for restoring the memorized shape is not degraded. The bending members are not forcibly deformed in the sterilizer, and thus an accident caused by damage to the insertion portion of the endoscope can be prevented. In addition, since bending members 44A and 44B comprise thin plates, a larger restoration force can be assured, as compared with an SMA having a diameter, e.g., 0.15 to 0.25 mm, corresponding to the thickness of the thin plate. In order to obtain the same restoration force as in the bending member of a thin plate by using a wire-like SMA, the diameter of the SMA must be naturally increased. As a result, the bending members occupy the space near the central portion (FIG. 2) to urge other members, e.g., image guide fibers 16 and light guide fibers 18.

In this embodiment, bending members 44A and 44B can be located near the inner wall surfaces of joint pieces 10 of bending pipe section 6, and the central space of insertion portion 2 can be assured.

Figures 4, 5, 6:
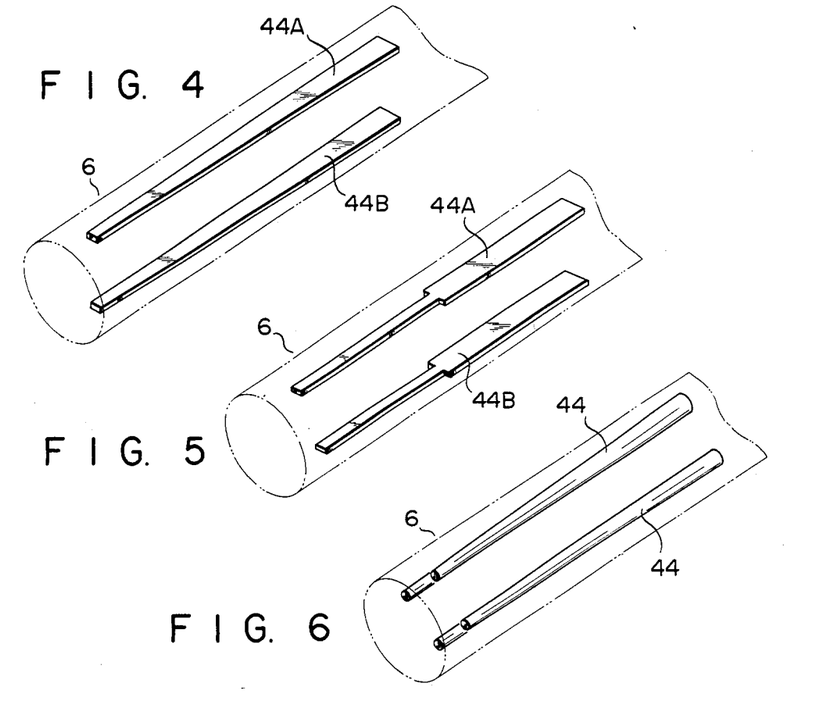
FIG. 4 is a perspective view showing a first modification of a drive member according to the first embodiment.
FIG. 5 is a perspective view showing a second modification of the drive member.
FIG. 6 is a perspective view showing a third modification of the drive member.

FIG. 4 shows a first modification of the bending member according to this embodiment. In this modification, bending members 44A and 44B are tapered toward their distal ends. By using these bending members and upon energization of one bending member, the sectional area of the distal end portion of the other bending member is small, and the other bending member can be easily deformed. A shape restoration rate, i.e., a bending rate can be increased. Bending of the insertion portion is started from the distal end of bending pipe 6. For this reason, the bending pipe can be easily bent in a very narrow body cavity and can be easily inserted.

A second modification of the first embodiment is shown in FIG. 5.

In this modification, the front and rear end portions of bending members 44A and 44B have two different widths; each front end portion is narrower than the rear end portion. Therefore, in this modification, the bending members can be bent in two steps, thereby providing an additional advantage compared to the previous modification.

A third modification of the first embodiment is shown in FIG. 6.

In this modification, bending members 44 of tapered round rods are used. In addition to the upper and lower bending members, right and left bending members identical with the upper and lower bending members are disposed in bending pipe section 6. A total of four bending members are disposed in bending pipe section 6, so that pipe section 6 can also be bent in the right or left direction. In this modification, since the individual bending members are made of rods, the bending pipe can be easily bent in any one of the four directions.

The bending member is not limited to the ones described in the above embodiment and modifications.

For example, a bending member can comprise a coil and be heated to contract, thereby bending the bending pipe section. In addition, electric power need not be used to heat the bending member. For example, hot water or air may be used, or any other heating member may be used.

Figure 7:
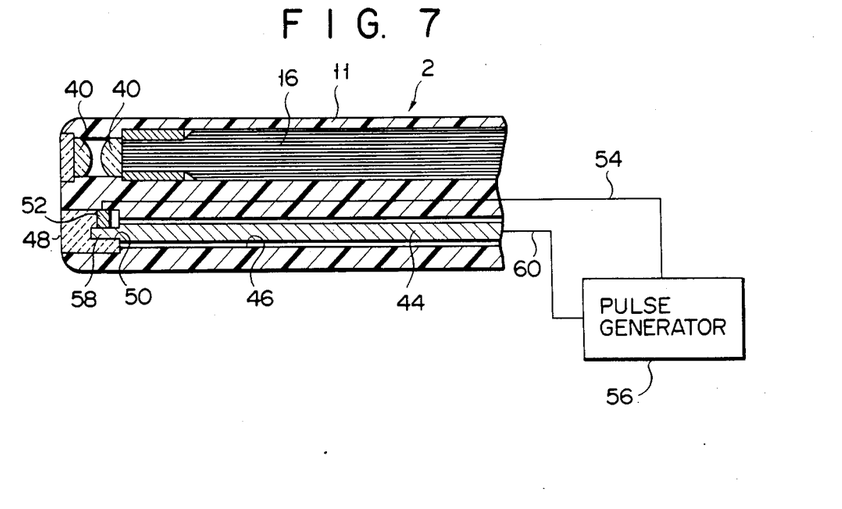
FIG. 7 is a longitudinal sectional view schematically showing a medical tube according to a second embodiment of the present invention.
Figure 8:
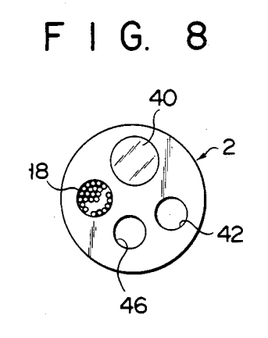
FIG. 8 is a front view of a tube shown in FIG. 7.

A second embodiment of the present invention will be described with reference to FIGS. 7 to 10. FIG. 7 shows insertion portion 2 of the endoscope using a medical tube according to the second embodiment. Light guide fibers 18 and image guide fibers 16 are inserted in outer tube 11 along its entire length. The distal end faces of the image guide fibers 16 oppose objective optical system 40 arranged at the distal end portion of insertion portion 2.

Insertion portion 2 includes first channel 42 for inserting a treatment tool and second channel 46, or storage means, for receiving bending or drive member 44. Holding member 48 made of an electrically insulating material such as ceramic or synthetic resin is mounted on the distal end of second channel 46. Recess 50 is formed at the rear end face of holding member 48, and electrical contact 52 is formed on one of the side walls of recess 50. One end of first lead wire 54 is connected to contact 52, and the other end of lead wire 54 is connected to pulse generator 56.

Figure 9:
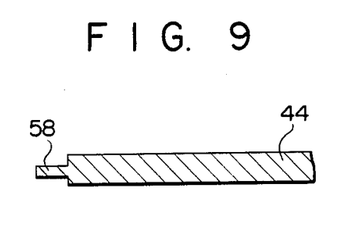
FIG. 9 is an enlarged sectional view of a front section of a drive member according to the second embodiment.

In the second embodiment, as shown in FIG. 9, drive member 44 is made of a rod-like shape memory alloy such as a Ti-Ni alloy or a Cu-Zn-Al alloy. Flat fitting portion 58 is detachably fitted in recess 50 of holding member 48. When drive member 44 is inserted in second channel 46 and fitting portion 58 is fitted in recess 50, drive member 44 is held in channel 46. However, when drive member 44 is pulled to disengage fitting portion 58 from recess 50, drive member 44 can be removed from channel 46. In fine, drive member 44 is detachably mounted in second channel 46.

Figure 10:
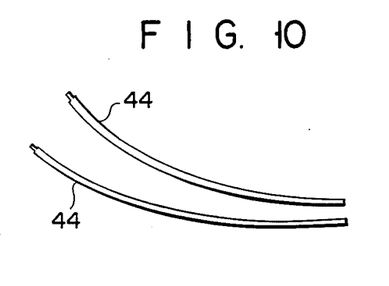
FIG. 10 is a perspective view of the drive member.

One end of second lead wire 60 is connected to the proximal end portion of drive member 44, and the other end of lead wire 60 is connected to pulse generator 56. Therefore, drive member 44 can be energized and heated by pulse generator 56. Drive member 44 is designed to memorize a shape so as to be bent upon heating. Transformation point (Af), i.e., the austenite phase transformation end temperature is set to be 45° C. slightly higher than a body temperature. Drive member 44 includes a plurality of members having different bending amounts, as shown in FIG. 10.

In this embodiment, insertion portion 2 comprises outer tube 11, that is, a multilumen tube made of polyurethane or silicone resin. Insertion portion 2 is bent together with drive member 44.

The operation of the insertion portion of the endoscope according to the second embodiment will be described below.

Insertion portion 2 of the endoscope is inserted in a body cavity such as a blood vessel. In order to deform insertion portion 2 to change the direction of view, pulse generator 56 is energized to supply a pulse current to drive member 44. Drive member 44 is heated due to its electrical resistance and is bent when it is heated to a temperature higher than the (Af) point. At this time, insertion portion 2 is also bent. In other words, insertion portion 2 can be bent by drive member 44. By selectively using drive members 44 having different bending amounts, the bending amount of insertion portion 2 can be increased or decreased. Since drive member 44 can be detachably mounted in insertion portion 2, the bending amount of insertion portion 2 can be changed by using drive member 44 having a desired bending amount.

In the second embodiment, insertion efficiency of the endoscope and visibility during observation can be improved.

Drive member 44 may be mounted in second channel 46 after insertion portion 2 is inserted in a predetermined position of the body cavity. However, drive member 44 may be mounted in second channel 46 beforehand.

Figure 11:
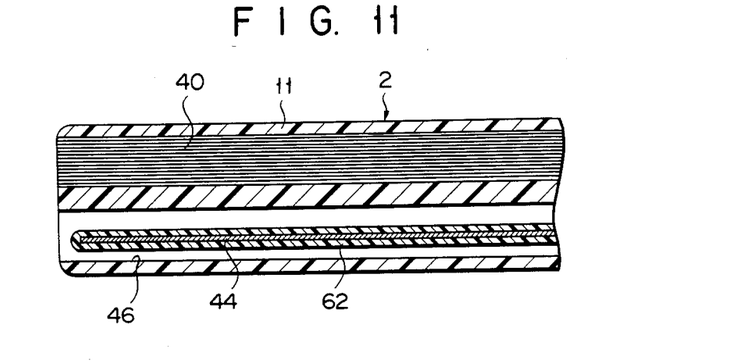
FIG. 11 is an enlarged sectional view of a front section of a tube and a first modification of the drive member of the second embodiment.
Figure 12:
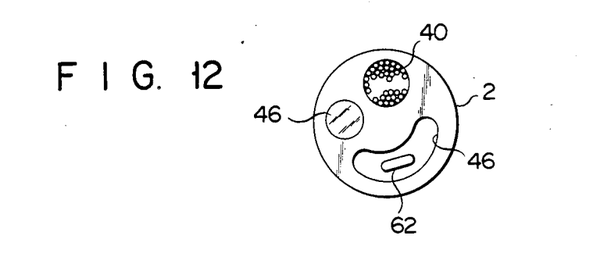
FIG. 12 is a front view of the tube shown in FIG. 11.
Figure 13:
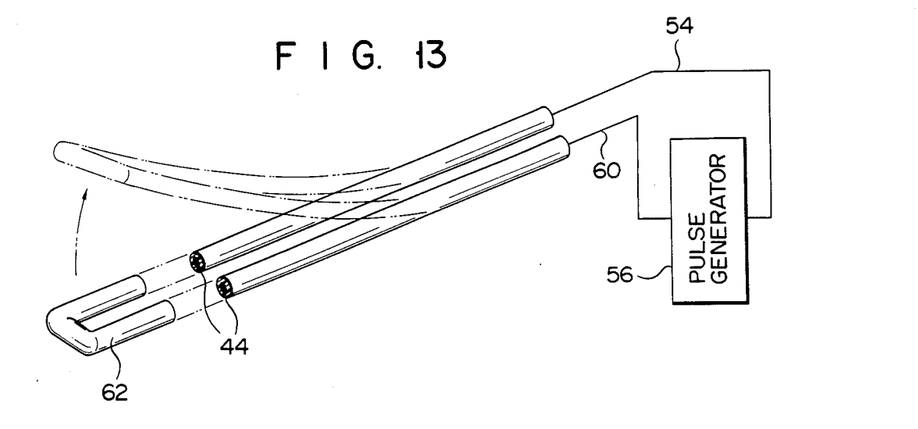
FIG. 13 is a schematic perspective view showing a state wherein the drive member of the first modification is bent.

FIGS. 11 to 13 show a first modification of the drive member of the second embodiment. In this modification, drive member 44 comprises a substantially U-shaped member coated with insulating layer 62 made of silicone rubber or ceramic. Drive member 44 is inserted in second channel 46 but is not fixed therein. Both ends of drive member 44 are respectively connected to pulse generator 56 through first and second lead wires 54 and 60, respectively.

In this modification, drive member 44 can be energized, heated, and bent. However, since the distal end portion of second channel 46 is open, physiological saline heated to a predetermined temperature may be supplied to channel 46 to heat drive member 44.

Figure 14:
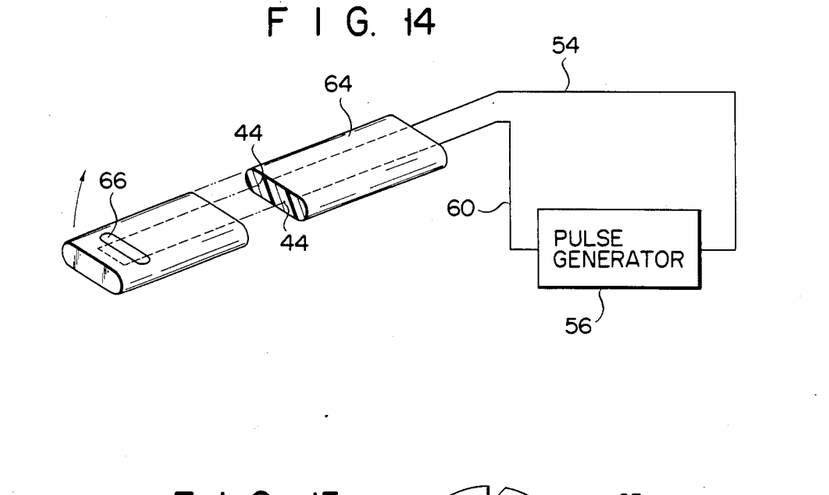
FIG. 14 is a schematic perspective view of a second modification of the drive member of the second embodiment.
Figure 15:
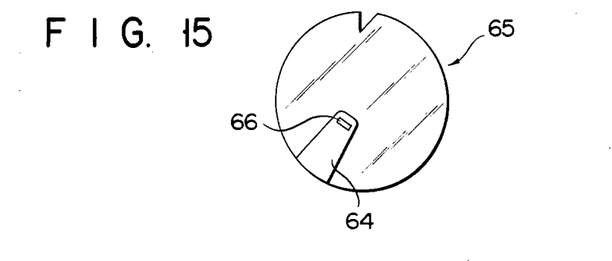
FIG. 15 is a front view showing a scope eyepiece arranged in the tube of the second embodiment.

FIGS. 14 and 15 show a second modification of drive member 44 of the second embodiment. In this modification, substantially U-shaped drive member 44 is embedded in plate-like insulating layer 64 made of silicone rubber. Mark 66 representing a bending direction of drive member 44 is attached to the distal end portion of insulating layer 64.

As shown in FIG. 15, mark 66 appears in the field of view of eyepiece 65 of the endoscope, and the bending direction of drive member 44 is not mistaken at the time of attachment.

Figure 16:
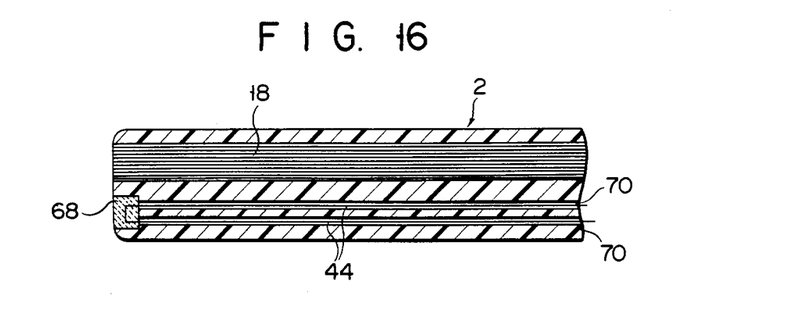
FIG. 16 is a longitudinal sectional view of a front section of a tube and a third modification of the drive member of the second embodiment.
Figure 17:
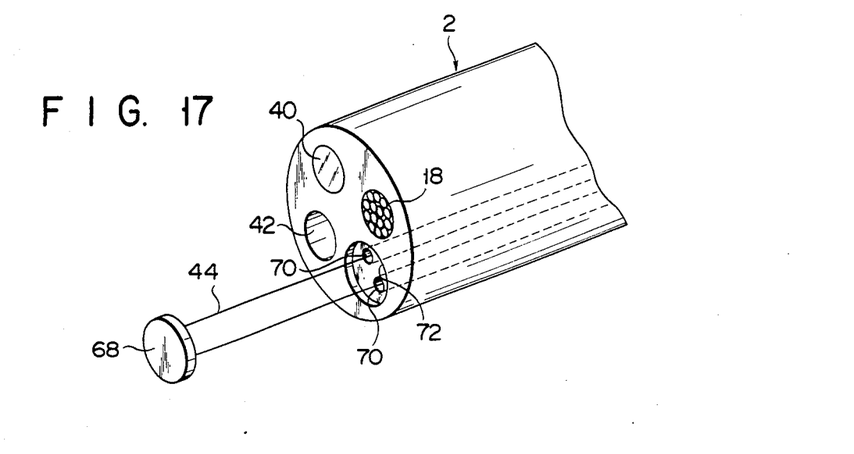
FIG. 17 is an enlarged perspective view of a distal end portion of the tube shown in FIG. 16.

FIGS. 16 and 17 show a third modification of the drive member. In this modification, distal end member 68 comprising an insulating member of a material such as ceramic or silicone rubber is mounted on the distal end portion of drive member 44. A pair of through holes 70 are formed in insertion portion 2 so as to receive drive members 44 therein. Recess 72 is formed at distal end of insertion portion 2 to detachably receive distal end member 68. In this modification, drive member 44 can be attached to or detached from through holes 70 of insertion portion 2.

Figure 18:
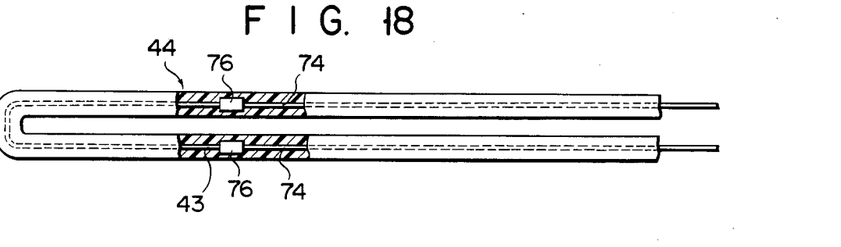
FIG. 18 is a partial cutaway plan view showing a fourth modification of the drive member.
Figure 19:
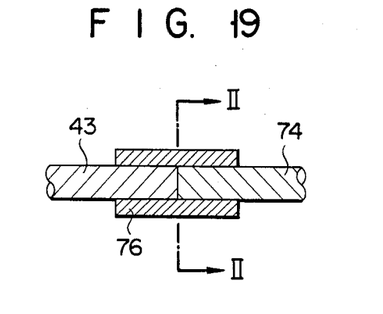
FIG. 19 is an enlarged sectional view showing a joint portion of the drive member shown in FIG. 18.
Figure 20:
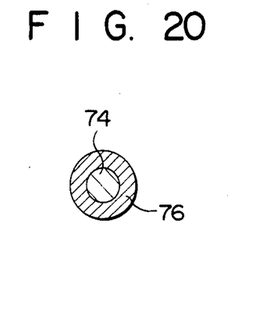
FIG. 20 is a sectional view of the drive member joint portion of FIG. 19 taken along the line II—II thereof.

FIGS. 18 to 20 show a fourth modification of the drive member. In this modification, substantially U-shaped drive member 44 is used in the same manner as in the above modification. However, shape memory alloy 43 is attached to only the distal end portion of drive member 44. Wire 74 such as a conductor is connected to this SMA through short tubular coupling 76.

Coupling 76 may be fixed by bonding or caulking to a joint portion between SMA 43 and wire 74. The following method may also be utilized. Coupling 76 may be made of a shape memory alloy, and SMA transformation point (Af) is set to be a temperature, e.g., 0° C., lower than room temperature. A circular shape having an inner diameter smaller than the outer diameter of SMA 43 is memorized in coupling 76. At the time of assembly, coupling 76 is deformed to increase the inner diameter at a temperature lower than the (Af) point, e.g., −10° C. SMA 43 and wire 74 are inserted inside coupling 76. Coupling 76 is then heated to a temperature higher than the (Af) point and shrinks to couple SMA 43 and wire 74.

In the second embodiment described above, the level of a pulse current supplied to drive member 44 may be adjusted to control the bending amount of drive member 44 up to a maximum bending amount. A shape may be memorized in drive member 44 only for a length enough to bend insertion portion 2. The coupling structure of the fourth modification may be applied to other embodiments and other modifications.

A medical tube according to a third embodiment of the present invention will be described with reference to FIGS. 21 and 22.

Figures 21, 22:
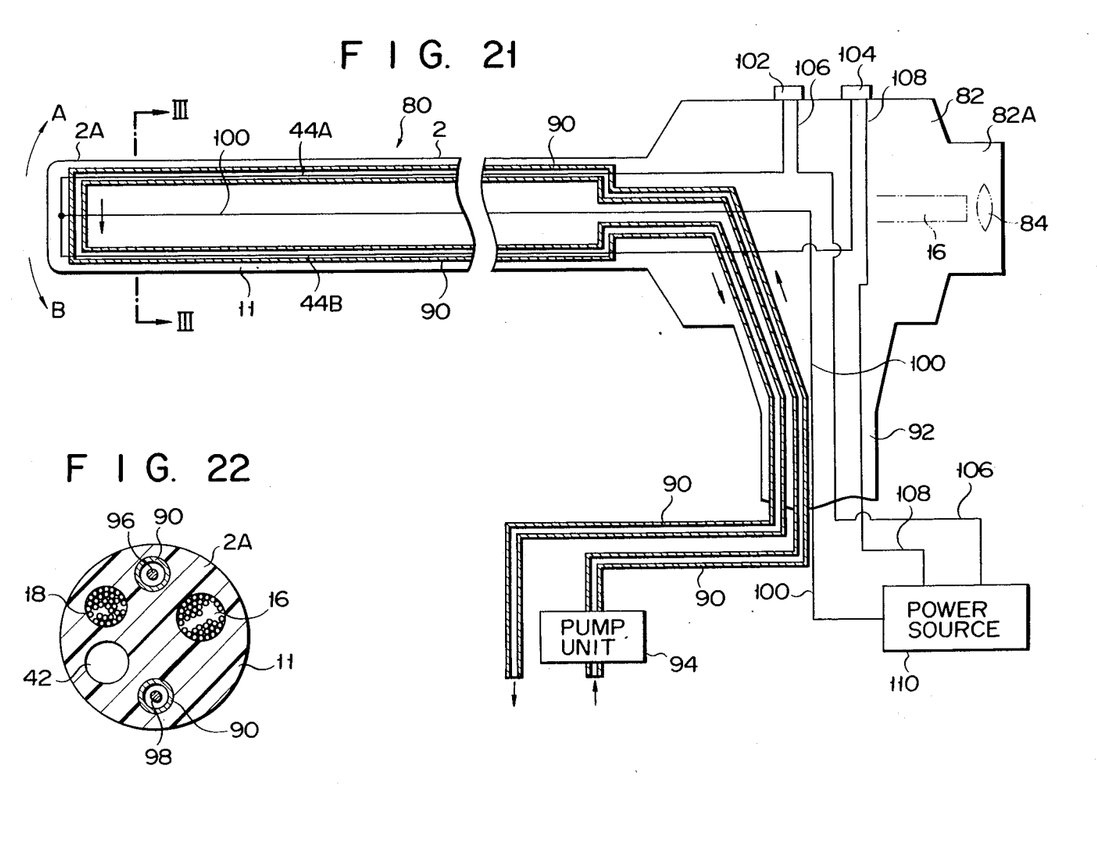
FIG. 21 is a schematic longitudinal sectional view of a medical tube according to a third embodiment of the present invention.
FIG. 22 is a sectional view of the tube shown in FIG. 21 taken along the line III—III thereof.

Endoscope 80 shown in FIG. 21 comprises insertion portion 2 and operation portion 82. Insertion portion 2 has a medical tube according to the third embodiment, and operation portion 82 is connected to the proximal end of insertion portion 2. A body or outer tube 11 of insertion portion 2 is made of, e.g., synthetic resin. As shown in FIG. 22, image guide fibers 16, light guide fibers 18, and channel 42 for receiving a treatment tool are inserted in outer tube 11 along its entire length. One end face of each of image guide fibers 16 is attached to optical system 40 (FIG. 7) arranged at distal end portion 2A of insertion portion 2. The other end face of each of image guide fibers 16 opposes eyepiece 84 arranged in eyepiece unit 82A of operation portion 82. One end of each of light guide fibers 18 is located at distal end portion 2A, and the other end thereof passes through operation portion 82 and is connected to a light source (not shown) having a lamp therein through a light guide cable, one end of which is connected to operation portion 82. Channel 42 for receiving a treatment tool has an opening at distal end portion 2A to constitute a treatment tool inlet port (not shown) in operation portion 82. Therefore, a treatment tool can be inserted in a body cavity from the insertion port through channel 42.

Pipe 90, or circulating means, is arranged in outer tube 11 of insertion portion 2 to supply a cooling liquid. One end of pipe 90 is connected to pump unit 94 through universal cord 92 of endoscope 80, and the other end of pipe 90 is led from insertion portion 2 to operation portion 82 and universal cord 92. The distal end as the other end of pipe 90 is open to the air. Pump unit 94 serves as an air supply pump to supply air into pipe 90.

Shape memory alloy wires, i.e., first and second drive members 44A and 44B are arranged in pipe 90 in outer tube 11. Each of wires 44A and 44B comprises a bidirectional bending wire which is bent in the A or B direction upon its heating to a temperature higher than the transformation temperature. This wire restores the original linear shape when it is cooled to a temperature lower than the transformation temperature. In this embodiment, the transformation temperature is set to be a temperature higher than a body temperature.

Both ends of drive members 44A and 44B are fixed inside outer tube 11. The distal ends of drive members 44A and 44B are connected to lead wire 100, and the rear ends of members 44A and 44B are electrically connected to first and second bending operation switches 102 and 104 arranged in operation portion 82, respectively. Lead wires 106 and 108 are led from operation switches 102 and 104 and are connected to power source 110 together with lead wire 100 through universal cord 92.

The operation of distal end portion 2A of the insertion portion of the endoscope will be described below.

In order to insert distal end portion 2A of insertion portion 2 in endoscope 80 into a portion of interest in the body cavity and to bend distal end portion 2A in the A direction in FIG. 21, first bending operation switch 102 is turned on to energize first drive member 44A. Drive member 44A is heated to a temperature higher than the transformation temperature and is bent in the A direction. Since both ends of drive member 44A are fixed inside outer tube 11 of insertion portion 2, distal end portion 2A of insertion portion 2 is also bent in the A direction.

In order to straighten insertion portion 2 or bend it in the B direction, pump unit 94 is energized to supply a cooling fluid to pipe 90 to cool drive member 44A to a temperature below the transformation temperature. As a result, drive member 44A restores the original shape, i.e., straight, and insertion portion 2 also restores the straight shape.

In order to bend insertion portion 2 in the B direction, second bending operation switch 104 is closed to energize and heat second drive member 44B.

In the above endoscope, after drive members 44A and 44B arranged in pipe 90 of insertion portion 2 are energized and heated, a cooling gas is supplied to pipe 90 to immediately cool the drive members in a short period of time, thereby immediately causing the drive members to restore the original shape.

Four drive members may be used to bend insertion portion in any one of four directions.

Instead of using electric power, warm water or air may be supplied to circulating means to heat and deform the drive members.

Figure 23:
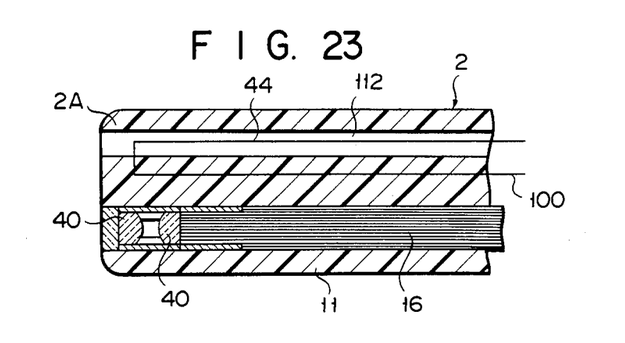
FIG. 23 is an enlarged sectional view of a front section of a tube, and showing a first modification of a cooling liquid supply pipe according to the third embodiment of the present invention.

FIG. 23 shows a modification of a cooling fluid supply pipe according to the third embodiment.

A typical cardiac endoscope is used to spray physiological saline from the distal end portion of the endoscope so as to assure the field of view. Blood is temporarily removed from the distal end portion of the endoscope. Meanwhile, the portion of interest is observed.

In this modification, pipe 112 for supplying a cooling fluid is open at distal end portion 2A, and the shape memory alloy, i.e., drive member 44 is bent near distal end portion 2A and is fixed in outer tube 11 of insertion portion 2. Lead wire 100 is connected to one end of member 44. Image guide fibers 16 and observation optical system 40 are arranged in outer tube 11 of insertion portion 2.

In this modification, drive member 44 is energized and heated, or physiological saline is supplied to pipe 112 to cool drive member 44. Insertion portion 2 can then be quickly bent. In this modification, the spraying hole of physiological saline and a cooling fluid pipe are constituted by a single pipe, and thus the outer diameter of the insertion portion of the endoscope can be decreased.

Figure 24:
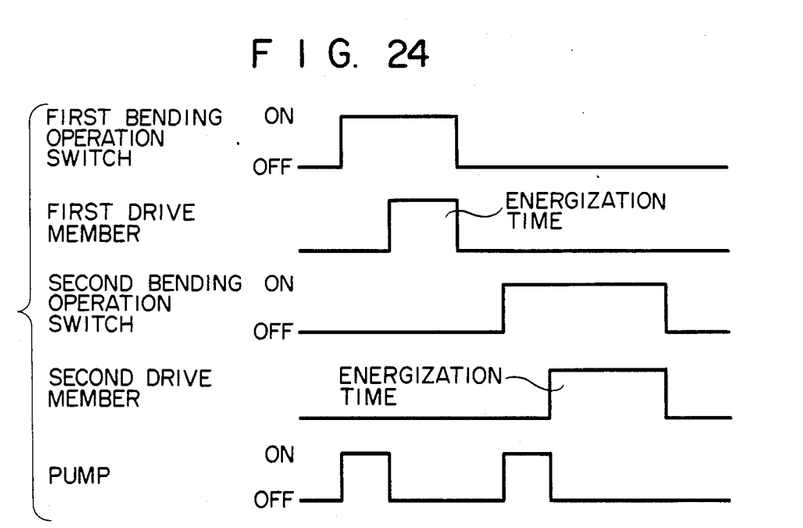
FIG. 24 is a timing chart for explaining a control circuit of an endoscope with the medical tube according to the third embodiment.

In the third embodiment and its modification, pump unit 94 may be driven in synchronism with first and second bending operation switches 102 and 104, as shown in the timing chart of FIG. 24. For example, when the first bending operation switch is closed, the pump is synchronously operated, and thereafter the first drive member is energized.

Figure 25A:
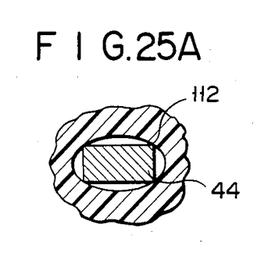
FIGS. 25A to 25C are sectional views, each showing modification of the pipe and the drive member inserted in the pipe according to the third embodiment.
Figure 25B:
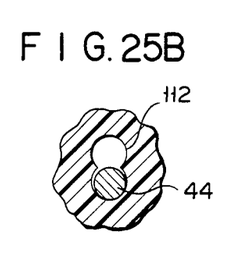
Figure 25C:
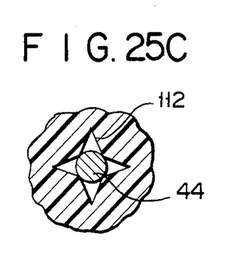

As shown in FIGS. 25A to 25C, the shapes of drive member 44 and pipe 112 are changed to allow rotation of drive member 44 within pipe 112. In this case, drive member 44 is designed not to be bent in a direction excluding a predetermined direction.

An electrical resistance of the drive member may be detected by a detector to obtain a bending amount, and the pump is driven until the drive member is straightened.

A plurality of drive members having different bending amounts may be prepared and selectively inserted in the pipe as needed.

Insertion portions which respectively correspond to the drive members may be formed in the outer tube.

In the third embodiment, the pipe is arranged in the insertion portion of the endoscope to supply a cooling fluid, and the drive member is arranged in the pipe. The drive member can be quickly cooled to a temperature below the transformation temperature. As a result, the insertion portion of the endoscope can be quickly bent.

What is claimed is:

1. A medical tube to be inserted in a body cavity, comprising:
    an outer tube having a front section; and
    a drive member arranged at said front section, and having an elongated shape memory alloy adapted to have a transformation temperature which is set to be not less than 60° C. such that a memorized shape is restored at a temperature higher than a temperature of heat of 55° C. to 60° C. applied to said shape memory alloy during sterilization of said medical tube.

2. A medical tube according to claim 1, wherein said drive member has a thin plate shape.

3. A medical tube according to claim 1, wherein said drive member has a distal end portion whose sectional area is smaller than that of a proximal end portion thereof.

4. A medical tube according to claim 1, wherein drive members are respectively arranged at both sides of an inner surface of said outer tube, thereby selectively bending said front section of said outer tube in two directions.

5. A medical tube according to claim 1, wherein drive members are respectively disposed in upper, lower, right, and left inner wall surface portions of said outer tube, thereby selectively bending said front section of said outer tube in four directions.

6. A medical tube according to claim 1, further comprising storage means arranged in said outer tube, said storage means being provided with openings at distal and rear end portions of said outer tube and being adapted to store said drive member therein.

7. A medical tube according to claim 6, wherein said drive member is detachably mounted inside said storage means, said outer tube being bent at a desireable angle by selecting said drive member to have the desireable angle from among a plurality of drive members bendable at different angles.

8. A medical tube according to claim 7, further comprising a closing member attached to a distal end of said drive member for closing said distal end opening of said outer tube in a water-tight manner when said drive member is stored in said storage means.

9. A medical tube according to claim 6, wherein said drive member is inserted inside said storage means.

10. A medical tube according to claim 6, wherein said drive member has a mark at one side surface of a distal end portion thereof, the mark being adapted to represent a bending direction of said drive member.

11. A medical tube according to claim 1, further comprising circulating means arranged inside said outer tube and extending from said front section to a rear end portion of said outer tube, said circulating means being adapted to circulate a cooling fluid, said drive member being housed inside said circulating means.

12. A medical tube according to claim 11, wherein said circulating means has an opening at said distal end portion of said outer tube.

13. A medical tube according to claim 1, further comprising a pulse generator connected to an end portion of said drive member.

14. A medical tube to be inserted in a body cavity, comprising:
    an outer tube having distal and rear end portions,
    storage means arranged in said outer tube and having openings at front and rear end portions of said outer tube, said storage means being adapted to store a drive member; and
    a drive member for bending said tube, detachably mounted inside said storage means and including a pair of shape memory alloy segments electrically connected with each other at their distal ends.

15. A medical tube according to claim 14, further comprising circulating means arranged inside said outer tube and extending from said front portion to a rear end portion of said outer tube, said circulating means being adapted to circulate a cooling fluid, said drive member being housed inside said circulating means.

16. A medical tube according to claim 15, wherein said circulating means has an opening at said distal end portion of said outer tube.

* * * * *